(12) United States Patent
Zhou

(10) Patent No.: US 11,875,909 B2
(45) Date of Patent: Jan. 16, 2024

(54) PULSE GENERATOR AND RADIATION SYSTEM HAVING THE SAME

(71) Applicant: SHANGHAI UNITED IMAGING HEALTHCARE CO., LTD., Shanghai (CN)

(72) Inventor: Chenglong Zhou, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 188 days.

(21) Appl. No.: 17/448,045

(22) Filed: Sep. 18, 2021

(65) Prior Publication Data

US 2022/0093284 A1 Mar. 24, 2022

(30) Foreign Application Priority Data

Sep. 21, 2020 (CN) .......................... 202022084885.1

(51) Int. Cl.
*G21K 1/04* (2006.01)
*A61B 6/00* (2006.01)
*A61B 6/10* (2006.01)

(52) U.S. Cl.
CPC .............. *G21K 1/046* (2013.01); *A61B 6/107* (2013.01); *A61B 6/54* (2013.01)

(58) Field of Classification Search
CPC . G21K 1/02; G21K 1/043; H05G 1/56; G03B 9/08; A61B 6/06; A61B 6/035; A61B 6/40; A61B 6/405; A61B 2017/00154
See application file for complete search history.

(56) References Cited

FOREIGN PATENT DOCUMENTS

WO WO-2016196521 A1 * 12/2016 ............... A61B 6/02

* cited by examiner

*Primary Examiner* — Don K Wong
(74) *Attorney, Agent, or Firm* — METIS IP LLC

(57) ABSTRACT

Pulse generators and radiation systems having the same are provided. A pulse generator may include a shielding device and a control device operably connected with the shielding device. The control device may be configured to control the shielding device to intermittently shield radiation emitted from the radiation source to produce pulsed radiation.

20 Claims, 5 Drawing Sheets

PULSE GENERATOR AND RADIATION SYSTEM HAVING THE SAME

CROSS-REFERENCE TO RELATED APPLICATIONS

This application claims priority to Chinese Patent Application No. 202022084885.1, filed on Sep. 21, 2020, the contents of which are hereby incorporated by reference.

TECHNICAL FIELD

The present disclosure generally relates to radiation technology, and more particularly, to pulsed radiation sources.

BACKGROUND

Pulsed radiation sources are widely used in medical devices. Existing pulsed radiation sources often install a grid electrode on an electron beam path, and apply a negative pulsed voltage to the grid electrode to generate pulsed radiation. However, existing pulsed radiation sources are complex, which results in high costs for manufacture, operation, and/or maintenance. Therefore, it is desirable to provide pulsed radiation sources with a simple structure.

SUMMARY

According to a first aspect of the present disclosure, a pulse generator is provided. The pulse generator may include a shielding device and a control device operably connected with the shielding device. The control device may be configured to control the shielding device to intermittently shield radiation emitted from the radiation source to produce pulsed radiation.

In some embodiments, the shielding device may include a rotary table configured to rotate about a center of the rotary table, and a plurality of leaves circumferentially extending from the rotary table.

In some embodiments, a leaf of the plurality of leaves has a first absorption coefficient, an area between two neighboring leaves of the plurality of leaves with a second absorption coefficient, and the first absorption coefficient is greater than the second absorption coefficient.

In some embodiments, the rotary table has the first absorption coefficient.

In some embodiments, a thickness and a first absorption coefficient of each leaf of the plurality of leaves relate to an intensity of the radiation emitted from the radiation source.

In some embodiments, a size of each leaf of the plurality of leaves is configured for shielding the radiation emitted from the radiation source.

In some embodiments, a projection position of the center of the rotary table is offset from a center of the radiation source, the projection position of the center of the rotary table being a position of a projection of the center of the rotary table onto a plane of the radiation source.

In some embodiments, the shielding device may include a rail parallel to an emission window of the radiation source; and a leaf configured to slide along the rail, the leaf being made of a radiation impermeable material.

In some embodiments, a size of the leaf is configured for shielding the radiation emitted from the radiation source.

In some embodiments, the shielding device may include a retractable module operably connected to a leaf, the retractable module being controlled by the control device to extend and retract the leaf along a direction parallel to an emission window of the radiation source, the leaf being made of a radiation impermeable material.

In some embodiments, a size of the leaf is configured for shielding the radiation emitted from the radiation source.

In some embodiments, the control device may include a motor configured to drive the shielding device, or a portion thereof, to intermittently shield the radiation emitted from the radiation source.

In some embodiments, a projection position of the motor projected onto a plane of the radiation source is offset from the radiation source.

In some embodiments, the control device may include a frequency converter operably connected to the motor, the frequency converter being configured to control a speed of the shielding device, or a portion thereof.

In some embodiments, a projection position of the frequency converter projected onto a plane of the radiation source is offset from the radiation source.

In some embodiments, the radiation emitted from the radiation source includes X-ray, and a material of the shielding device, or a portion thereof, includes at least one of iron, tungsten, lead, a tungsten alloy, or a lead alloy.

In some embodiments, a surface of the shielding device is parallel to a surface of an emission window of the radiation source.

According to another aspect of the present disclosure, a system is provided. The system may include a radiation source and a pulse generator. The pulse generator may include a shielding device and a control device operably connected with the shielding device. The control device may be configured to control the shielding device to intermittently shield radiations emitted from the radiation source to produce pulsed radiation.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments.

These exemplary embodiments are described in detail with reference to the drawings.

The drawings are not to scale. These embodiments are non-limiting exemplary embodiments, in which like reference numerals represent similar structures throughout the several views of the drawings, and wherein:

FIG. 1 is a schematic diagram illustrating an exemplary radiation system according to some embodiments of the present disclosure;

FIG. 2 is a block diagram illustrating an exemplary radiation system according to some embodiments of the present disclosure;

FIG. 3 is a block diagram illustrating an exemplary pulse generator according to some embodiments of the present disclosure;

FIG. 4 is a block diagram illustrating an exemplary pulse generator according to some embodiments of the present disclosure;

FIG. 5 is a schematic diagram illustrating an exemplary pulse generator according to some embodiments of the present disclosure;

FIG. 6 is a schematic diagram illustrating an exemplary radiation system according to some embodiments of the present disclosure;

FIG. 7 is a schematic diagram illustrating an exemplary shielding device according to some embodiments of the present disclosure; and FIG. 8 is a block diagram illustrating an exemplary shielding device according to some embodiments of the present disclosure.

DETAILED DESCRIPTION

Figure 1:
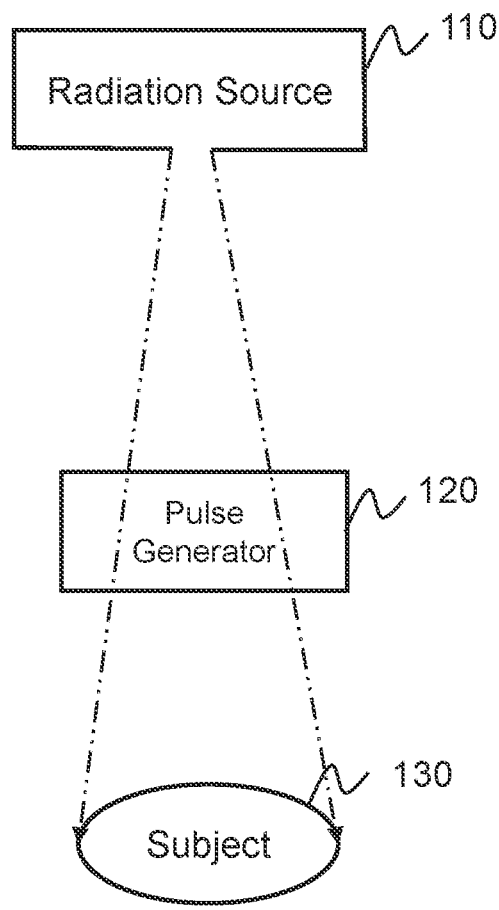

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The object may include a biological object and/or a non-biological object. The biological object may be a human being, an animal, a plant, or a portion thereof (e.g., a cell, a tissue, an organ, etc.). In some embodiments, the object may be a man-made composition of organic and/or inorganic matters that are with or without life.

Provided herein are pulse generators and radiation systems having the same. The radiation systems may emit radiation including neutron, proton (e.g., α-ray), electron (e.g., β-ray), μ-meson, heavy-ion, X-ray, γ-ray, ultraviolet, laser, or the like, or any combination thereof. In some embodiments, the radiation systems may be imaging systems used in medical field or industrial field. Merely by way of example, the radiation emitted by a radiation system is X-ray, and a corresponding imaging system may include a computed tomography (CT) system, a digital radiography (DR) system, a multi-modality system, or the like, or a combination thereof. Exemplary multi-modality systems may include a computed tomography-positron emission tomography (CT-PET) system, a computed tomography-magnetic resonance imaging (CT-MRI) system, etc. As another example, the radiation system may be used in an inspection of an internal component including, for example, flaw detection, security scanning, failure analysis, metrology, assembly analysis, void detection, wall thickness analysis, or the like, or a combination thereof.

An aspect of the present disclosure relates to a pulse generator for a radiation source. The pulse generator may include a shielding device and a control device operably connected with the shielding device. The control device may be configured to control the shielding device to intermittently shield radiation emitted from the radiation source to produce pulsed radiation. Accordingly, the sample pulse generator may achieve a low cost of the radiation source.

FIG. 1 is a schematic diagram illustrating exemplary radiation system 100 according to some embodiments of the present disclosure. As shown in FIG. 1, the radiation system 100 may include a radiation source 110 and a pulse generator 120.

The radiation source 110 may be configured to emit radiation. In some embodiments, the radiation may include a particle ray, a photon ray, or the like, or a combination thereof. A particle ray may include neutron, proton (e.g., α-ray), electron (e.g., β-ray), μ-meson, heavy-ion, or the like, or a combination thereof. A photon ray may include X-ray, γ-ray, ultraviolet, laser, or the like, or a combination thereof. In some embodiments, the radiation source 110 may be a continuum source that emits continuous radiation. In some embodiments, the radiation source 110 may include a tube, an emission window, etc. The tube may be configured to emit radiation. For example, the tube may include a cold cathode ion tube, a high vacuum hot cathode tube, a rotating anode tube, or the like, or any combination thereof. The emission window may be configured as an outlet for radiation emission. The shape of the emission window may include a rectangle, a circle, a square, an irregular shape, or the like, or any combination thereof.

The pulse generator 120 may be configured to produce pulsed radiation. For example, the pulse generator 120 (or a portion thereof) may be mounted between the radiation source 110 and a subject 130 to be scanned. For example, the pulse generator 120 (or a portion thereof) may be mounted on a transmission path of the radiation emitted from the radiation source 110 to the subject 130. In some embodiments, the pulse generator 120 (or a portion thereof) may be mounted inside the radiation system 100 (e.g., an X-ray imaging system) via a bracket. In some embodiments, the pulse generator 120 (or a portion thereof) may be mounted close to the radiation source 110 to completely block the radiation emitted from the radiation source 110 towards the subject 130. For example, a diameter of the radiation beam impinging on pulse generator 120 increases along the transmission path of the radiation from the radiation source 110 towards the subject 130. Thus, a smaller size of a pulse generator 120 (or a portion thereof) may completely block the radiation beam emitted from the radiation source at a first point than that at a second point, in which the first point and the second point are both on the transmission path and the second point is more distant from the radiation source 110 than the first point. As used herein, completely blocking or shielding radiation emitted by a radiation source (e.g., the radiation source 110) indicates that the amount of radiation emitted by the radiation source that is blocked or shielded exceeds a threshold, e.g., 80%, 85%, 90%, 95%, etc. The amount of radiation that is blocked or shielded may be assessed based on a total amount of radiation emitted from the radiation source 110 and an amount of radiation that passes through the pulse generator 120. For example, the amount of radiation that is blocked or shielded may be a difference between the total amount of radiation emitted from the radiation source 110 and the amount of radiation that passes through the pulse generator 120. In the present disclosure, the term "blocking radiation" and the term "shielding radiation" are used interchangeably.

In some embodiments, the pulse generator 120 (or a portion thereof) may intermittently shield the continuous radiation emitted from the radiation source 110 to produce the pulsed radiation. For example, the pulse generator 120 may include a motion mechanism. During the movement of the motion mechanism, the pulse generator 120 (or a portion thereof) may completely block the radiation emitted from the radiation source 110 toward the subject 130 (such that the radiation emitted by the radiation source 110 does not impinge on the subject 130) at a moment, and the pulse generator 120 (or a portion thereof) may allow all or part of the radiation emitted from the radiation source 110 to traverse and travel toward the subject 130 (such that at least part of the radiation emitted by the radiation source 110 impinges on the subject 130) at a next moment. The blocking of the radiation and the transmission of the radiation may alternate, thereby generating pulsed radiation. For example, the pulse generator 120 may include a shielding device and a control device operably connected to the shielding device. As used herein, "operably connected" indicates that two or more components (e.g., devices, units, modules, etc.) are connected in any suitable manner for operation and/or communication, including wired, wirelessly, or some combination thereof. The control device may be configured to control the shielding device to intermittently shield radiation emitted from the radiation source to produce pulsed radiation. More descriptions of the exemplary pulse generator 120 may be found elsewhere in the present disclosure. See, e.g., FIGS. 3-4 and the descriptions thereof. More descriptions of the exemplary shielding device 210 may be found elsewhere in the present disclosure. See, e.g., FIGS. 4-5 and/or FIGS. 6-7 and the descriptions thereof. More descriptions of the exemplary control device 220 may be found elsewhere in the present disclosure. See, e.g., FIG. 3 and the descriptions thereof.

The subject 130 may be biological or non-biological. For example, the subject 130 may include a patient, a man-made object, etc. As another example, the subject 130 may include a specific portion, an organ, and/or tissue of the patient. For example, the subject 130 may include the head, the neck, the thorax, the heart, the stomach, a blood vessel, soft tissue, a tumor, nodules, or the like, or any combination thereof, of a patient.

It should be noted that the description of the radiation system 100 described in FIG. 1 is provided for the purposes of illustration, and not intended to limit the scope of the present disclosure. For persons having ordinary skills in the art, various variations and modifications may be conducted under the teaching of the present disclosure. However, those variations and modifications may not depart from the protection of the present disclosure. In some embodiments, the assembly and/or function of radiation system 100 may be varied or changed according to specific implementation scenarios. For example, the radiation source 110 and the pulse generator 120 may be integrated into one single device. As another example, some other components may be added into the radiation system 100, such as a detector, a processing device, a storage device, a terminal, a network, or the like, or a combination thereof.

Figure 2:
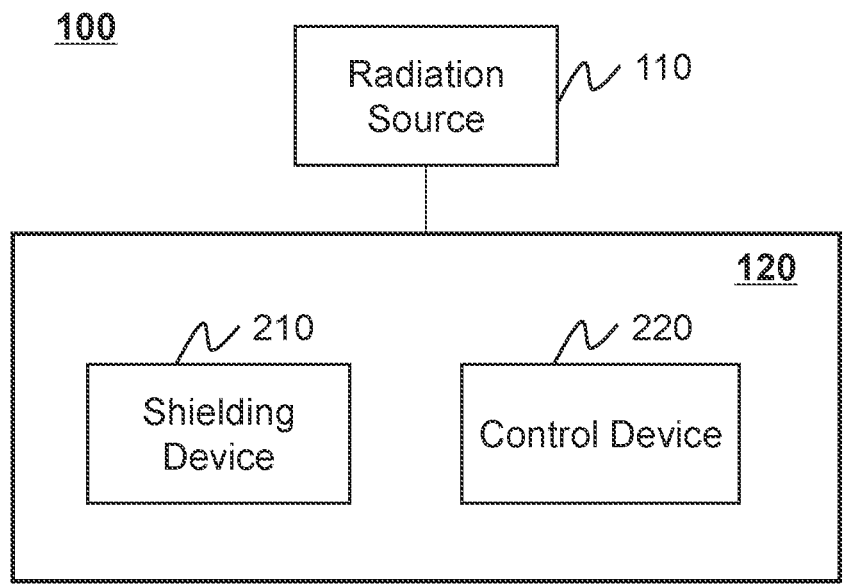

FIG. 2 is a block diagram illustrating an exemplary radiation system 100 according to some embodiments of the present disclosure. As shown in FIG. 2, the radiation system 100 may include the radiation source 110 and the pulse generator 120. The pulse generator 120 may include a shielding device 210 and a control device 220.

The shielding device 210 may be configured to intermittently shield the radiation emitted from the radiation source 110. The shielding device 120 may block and allow passage of the radiation emitted by the radiation source 110 alternately such that radiation intermittently impinges on a subject (e.g., the subject 130) positioned in the radiation transmission path but downstream to the pulse generator 120 (or a portion thereof, e.g., the shielding device 210). The alternation between blocking and allowing radiation passage by the shielding device 210 may occur at a regular interval or irregular intervals. Accordingly, the shielding device 210 neither continuously shields (or blocks) nor continuously allows passage of the radiation.

In some embodiments, the shielding device 210 may be of any shape, or any pattern, or any size, to realize intermittent radiation shielding. For example, the shielding device 210 may include a rotary table and a plurality of leaves circumferentially extending from the rotary table. The rotary table may be configured to rotate about a center of the rotary table. The plurality of leaves may be made of a radiation impermeable material. The plurality of leaves may distribute along a circumference of the rotary table. For example, an interval may be arranged between two neighboring leaves of the plurality of leaves. The rotation of the rotary table may drive the plurality of leaves to rotate. When the shielding device 210 rotates such that a leaf of the plurality of leaves is positioned in the transmission path of the radiation, the leaf may completely shield the radiation by completely absorbing or completely reflecting the incident radiation. When the shielding device 210 rotates such that an area between two neighboring leaves of the plurality of leaves is positioned in the transmission path of the radiation, at least a portion of the radiation may pass through the shielding device 210. As another example, the shielding device 210 may include a rail and a leaf. The leaf may be moveably mounted on the rail. The leaf may be configured to slide along the rail. When the leaf slides into the transmission path of the radiation, the leaf may completely shield the radiation. When the leaf slides out of the transmission path of the radiation, the radiation may pass through the shielding device 210 and travel toward the subject 130. As still another example, the shielding device 210 may include a leaf and a retractable module operably connected to the leaf. The retractable module may extend and retract the leaf. When the retractable module extends the leaf into the transmission path of the radiation, the leaf may completely shield the radiation. When the retractable module retracts the leaf out of the transmission path of the radiation, the radiation may pass through the shielding device 210 and travel toward the subject 130. As still another example, a size of a leaf may be configured for completely shielding the radiation emitted from the radiation source 110. As still another example, a shape of a leaf may include a rectangle, a circle, a square, a circular sector, an irregular shape, or the like, or any combination thereof. More descriptions of the exemplary shielding devices 210 may be found elsewhere in the present disclosure. See, e.g., FIGS. 3-4 and/or FIGS. 6-7 and the descriptions thereof.

In some embodiments, the shielding device 210, or a portion of the shielding device 210 (e.g., a leaf of the shielding device 210), may be made of a radiation impermeable material. As used herein, the term "radiation impermeable material" refers to a material that prevents the radiation emitted from the radiation source 110 to pass or diffuse through. The radiation impermeable material may absorb and/or reflect the radiation emitted from the radiation source 110. For example, the radiation emitted from the radiation source 110 is X-ray, and the material of the shielding device 210, or a portion of the shielding device 210 (e.g., a leaf of the shielding device 210), may include iron, tungsten, lead, a tungsten alloy, a lead alloy, or the like, or any combination thereof. As another example, the radiation emitted from the radiation source 110 is γ-ray, and the material of the shielding device 210, or a portion of the shielding device 210 (e.g., a leaf of the shielding device 210), may include iron, tungsten, lead, uranium, or the like, or any combination thereof.

In some embodiments, a surface of the shielding device 210 (or a portion thereof) may be parallel to a surface of an emission window of the radiation source 110 so as to facilitate the adjustment of a frequency of the produced pulsed radiation. In some embodiments, the frequency of the produced pulsed radiation may be adjusted by controlling a frequency (e.g., a rotation frequency, a stretching frequency, a sliding frequency, etc.) of the movement of the shielding device 210, or a portion thereof (e.g., a leaf of the shielding device 210). For example, an incident surface of a leaf on which the radiation impinges may be parallel to a surface of the emission window from which the radiation exits the radiation source 110. As another example, the surface of the shielding device 210 and the surface of an emission window that are parallel may be two surfaces between which the distance equals the shortest distance between the shielding device 210 and the radiation source 110. Alternatively, an incident surface of a leaf on which the radiation impinges may be not parallel to the surface of the emission window from which the radiation exits the radiation source 110.

The control device 220 may be configured to control one or more components of the shielding device 210. For example, the control device 220 may control one or more components (e.g., a leaf, a rotary table, a retractable module) of the shielding device 210 to intermittently shield radiation emitted from the radiation source 110 to produce pulsed radiation. In some embodiments, the control device 220 may control a frequency (e.g., a rotation frequency, a stretching frequency, a sliding frequency, etc.) of the movement of the shielding device 210, or a portion thereof (e.g., a leaf of the shielding device 210). The frequency of the shielding device 210, or the frequency of the leaf, may correlate with a frequency of the pulsed radiation. For example, the greater the frequency of the movement of the shielding device 210 (or the frequency of the movement of the leaf), the greater the frequency of the produced pulsed radiation.

In some embodiments, the control device 220 may include a motor, a frequency converter, a processor, a storage device (e.g., a memory), or the like, or any combination thereof. The motor may be configured to drive the shielding device 210 (or a portion thereof) to intermittently shield the radiation emitted from the radiation source 110. For example, the motor may be configured to drive a rotary table (and/or a leaf connected thereof) to rotate, a leaf to slide along a rail, a retractable module to extend and retract a leaf, etc. The frequency converter may be configured to control a speed of the movement of the shielding device (or a portion thereof). For example, the frequency converter may control a rotation speed of the motor, and/or control a frequency (e.g., a rotation frequency, an extending and retracting frequency, a sliding frequency, etc.) of the movement of a leaf of the shielding device 210. The processor may be configured to execute program instructions stored in the storage device to perform one or more functions of controlling the shielding device 210. Exemplary processor may include a central processing unit (CPU), an application-specific integrated circuit (ASIC), an application-specific instruction-set processor (ASIP), a graphics processing unit (GPU), a physics processing unit (PPU), a digital signal processor (DSP), a field programmable gate array (FPGA), a programmable logic device (PLD), a microcontroller unit, a microprocessor, an advanced RISC machines processor (ARM), or the like, or any combinations thereof. Exemplary memory may include a random access memory (RAM), a read only memory (ROM), or the like, or a combination thereof.

It should be noted that the description of the radiation system 100 described in FIG. 2 is provided for the purposes of illustration, and not intended to limit the scope of the present disclosure. For persons having ordinary skills in the art, various variations and modifications may be conducted under the teaching of the present disclosure. However, those variations and modifications may not depart from the protection of the present disclosure. In some embodiments, the assembly and/or function of radiation system 100 may be varied or changed according to specific implementation scenarios. For example, some other components may be added into the radiation system 100, such as a detector, a processing device, a storage device, a terminal, a network, or the like, or a combination thereof.

Figure 3:
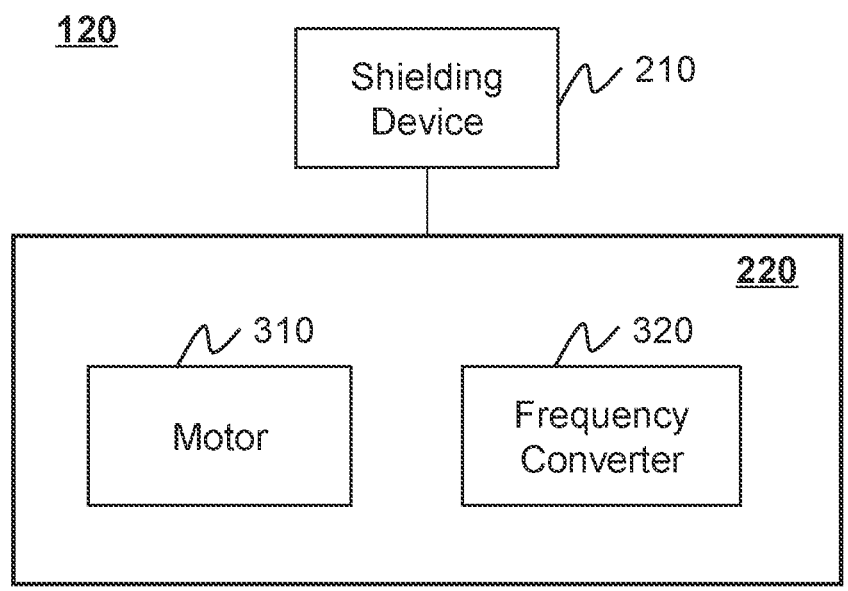

FIG. 3 is a block diagram illustrating an exemplary pulse generator 120 according to some embodiments of the present disclosure. As shown in FIG. 3, the pulse generator 120 may include a shielding device 210 and a control device 220. The control device 220 may include a motor 310 and a frequency converter 320 operably connected to the motor 310.

The motor 310 may be configured to drive the shielding device 210 (or a portion thereof) to move so as to intermittently shield the radiation emitted from the radiation source 110. The motor 310 may be a device that can convert one form of energy into mechanical energy and so imparts motion. Exemplary motors 310 may include an actuating motor, a servo-actuator, a servo motor, a stepping motor, a direct-current motor, an alternating-current motor, a synchronous motor, an asynchronous motor, or the like, or any combination thereof.

In some embodiments, the shielding device 210 may include a rotary table and a plurality of leaves circumferentially extending from the rotary table. The motor 310 may drive the rotary table (and/or one or more leaves connected thereof) of the shielding device 210 to rotate. When the shielding device 210 rotates such that a leaf of the plurality of leaves is positioned in the transmission path of the radiation, the leaf may completely shield the radiation by completely absorbing or completely reflecting the incident radiation. When the shielding device 210 rotates such that an area between two neighboring leaves of the plurality of leaves is positioned in the transmission path of the radiation, at least a portion of the radiation may pass through the shielding device 210. The rotation of the plurality of leaves may cause the radiation emitted from the radiation source 110 to be shielded intermittently, thereby generating pulsed radiation. In some embodiments, a rotation speed (or a rotation frequency) of the motor 310 may correlate with a frequency of the generated pulsed radiation. For example, the greater the rotation speed of the motor 310, the greater the frequency of the produced pulsed radiation.

In some embodiments, the shielding device 210 may include a rail and a leaf configured to slide along the rail. The motor 310 may drive the leaf to slide along the rail. When the leaf slides into the transmission path of the radiation, the leaf may completely shield the radiation. When the leaf slides out of the transmission path of the radiation, the radiation may pass through the shielding device 210 and travel toward to the subject 130. The slides of the leaf may cause the radiation emitted from the radiation source 110 to be shielded intermittently, thereby generating pulsed radiation. In some embodiments, a sliding frequency (e.g., a count of slides of the leaf to the transmission path of the radiation per unit time) of the leaf may correlate with a frequency of the generated pulsed radiation. For example, the greater the sliding frequency of the leaf driven by the motor 310, the greater the frequency of the produced pulsed radiation.

In some embodiments, the shielding device 210 may include a leaf and a retractable module operably connected to the leaf. The motor 310 may drive the retractable module to extend and retract the leaf. When the retractable module extends the leaf into the transmission path of the radiation, the leaf may completely shield the radiation. When the retractable module retracts the leaf out of the transmission path of the radiation, the radiation may pass through the shielding device 210 and travel toward the subject 130. The extending and retracting of the leaf may cause the radiation emitted from the radiation source 110 to be shielded intermittently, thereby generating pulsed radiation. In some embodiments, an extending and retracting frequency (e.g., a count of extending of the leaf to the transmission path of the radiation per unit time) of the leaf may correlate with a frequency of the generated pulsed radiation. For example, the greater the extending and retracting frequency of the leaf driven by the motor 310, the greater the frequency of the produced pulsed radiation.

In some embodiments, the motor 310 may be started before the radiation source 110 emits radiation. For example, the motor 310 may drive the shielding device 210 (or a portion thereof) to move (e.g., rotate, slide, extend or retract, etc.) before the radiation source 110 emits radiation. When the radiation source 110 emits radiation, the shielding device 210 (or a portion thereof) has been adjusted to a stable speed, thereby generating pulsed radiation of a stable or constant frequency.

The frequency converter 320 may be configured to control a speed (or a frequency) of the shielding device (or a portion thereof). The frequency converter 320 may be a motor drive to control a motor speed and/or torque by varying the motor input frequency and voltage of the motor 310. An exemplary frequency converter 320 may include a rectifier (e.g., converts alternating current (AC) to direct current (DC)), a filter configured to reduce and/or suppress electromagnetic interference generated by the frequency converter 320, an inverter (e.g., converts DC to AC), a brake unit configured to convert electrical energy into heat and consume the heat, a drive unit configured to drive a leaf to move (e.g., by way of rotation, sliding, etc.), a micro processing unit configured to process information relating to the frequency converter 320, or the like, or any combination thereof. In some embodiments, the frequency converter 320 may transmit the varied input frequency and voltage to the motor 310, then the speed of the motor 310 may be controlled, thereby the frequency of the generated pulsed radiation may be controlled.

It should be noted that the description of the pulse generator 120 described in FIG. 3 is provided for the purposes of illustration, and not intended to limit the scope of the present disclosure. For persons having ordinary skills in the art, various variations and modifications may be conducted under the teaching of the present disclosure. However, those variations and modifications may not depart from the protection of the present disclosure. In some embodiments, the assembly and/or function of pulse generator 120 may be varied or changed according to specific implementation scenarios.

Figure 4:
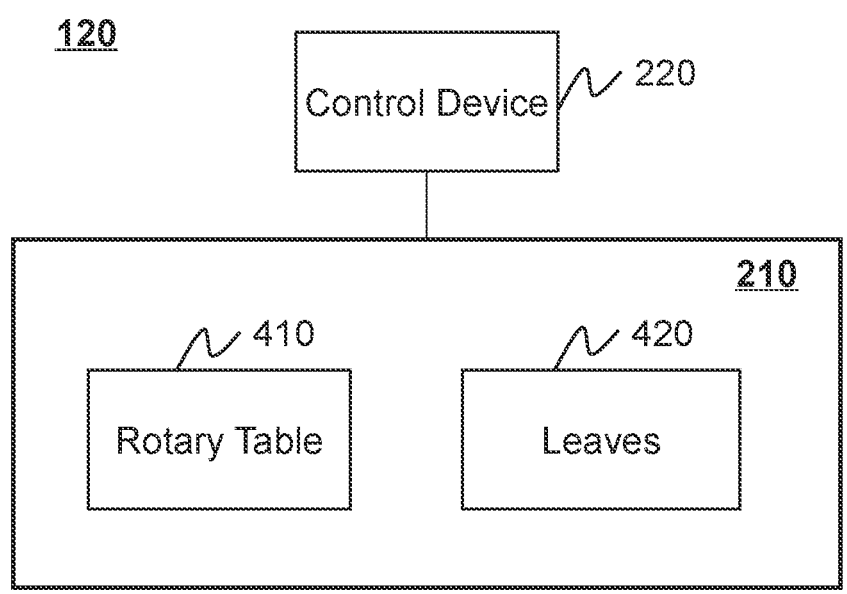
Figure 5:
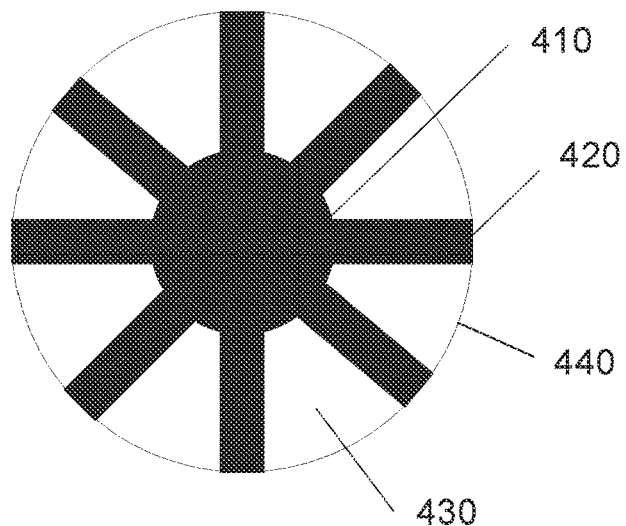

FIG. 4 is a block diagram illustrating an exemplary pulse generator 120 according to some embodiments of the present disclosure. As shown in FIG. 4, the pulse generator 120 may include a control device 220 and a shielding device 210. FIG. 5 is a schematic diagram illustrating an exemplary shielding device 210 according to some embodiments of the present disclosure. As shown in FIGS. 4 and 5, the shielding device 210 may include a rotary table 410 and a plurality of leaves 420.

The rotary table 410 may be configured to rotate driven by the control device 220 (e.g., the motor 310 thereof) about a point or an axis. For example, the rotary table 410 may rotate about a center or a rotation axis of the rotary table 410. As shown in FIG. 5, a shape of the rotary table 410 may be a circle. Alternatively, the shape of a rotary table 410 may be any suitable shape including e.g., a rectangle, a circle, a square, a circular sector, an irregular shape, or the like, or any combination thereof.

The plurality of leaves 420 may be attached to the rotary table 410 to rotate along with the rotary table 410. For example, as shown in FIG. 5, the plurality of leaves 420 may circumferentially extend from the rotary table 410, and one end of each leaf 420 that is away from the rotary table 410 may form a rotation trajectory 440. The plurality of leaves 420 may distribute along a circumference of the rotary table 410. For example, as shown in FIG. 5, an interval 430 may be arranged between two neighboring leaves of the plurality of leaves 420. In some embodiments, the plurality of leaves 420 may be made of a radiation impermeable material to prevent the radiation emitted from the radiation source 110 to pass or diffuse through.

In some embodiments, the rotary table 410 and the plurality of leaves 420 may be mounted between the radiation source 110 and a subject 130 to be scanned. For example, the rotary table 410 may be mounted inside the radiation system 100 (e.g., an X-ray imaging system) via a bracket. The plurality of leaves 420 may be mounted on a transmission path of the radiation emitted from the radiation source 110 to the subject 130. In some embodiments, the rotary table 410 and the plurality of leaves 420 may be mounted close to the radiation source 110, during the rotation of the plurality of leaves 420, each of the plurality of leaves 420, when positioned in the transmission path of the radiation, may completely block the radiation emitted from the radiation source 110 onto the subject 130. For example, when the shielding device 210 rotates such that a leaf of the plurality of leaves 420 is positioned in the transmission path of the radiation, the leaf may completely shield the radiation by completely absorbing or completely reflecting the incident radiation. When the shielding device 210 rotates such that an interval 430 between two neighboring leaves of the plurality of leaves 420 is positioned in the transmission path of the radiation, at least a portion of the radiation may pass through the shielding device 210. During the rotation of the plurality of leaves 420 along the rotary table 410, pulsed radiation may be produced.

In some embodiments, the plurality of leaves 420 may be made of a radiation impermeable material to prevent the radiation emitted from the radiation source 110 to pass or diffuse through. If the radiation emitted from the radiation source 110 is X-ray, exemplary radiation impermeable material may include iron, tungsten, lead, a tungsten alloy, a lead alloy, or the like, or any combination thereof. If the radiation emitted from the radiation source 110 is γ-ray, exemplary radiation impermeable material may include iron, tungsten, lead, uranium, or the like, or any combination thereof. In some embodiments, each of the plurality of leaves 420 may be made of a same material. Alternatively, some leaves of the plurality of leaves 420 may be made of a same material and others leaves of the plurality of leaves 420 may be made of a different material. For example, some leaves of the plurality of leaves 420 may be made of iron, others may be made of tungsten.

In some embodiments, the plurality of leaves 420 may be made of a material different from the material of at least one of the intervals 430. For example, each leaf of the plurality of leaves 420 may be made of a radiation absorbing material having a first absorption coefficient. An interval 430 between two neighboring leaves of the plurality of leaves 420 may be made of a radiation permeable (or semi-permeable) material having a second absorption coefficient. An absorption coefficient may reflect an absorption capacity of a material. A greater absorption coefficient may correspond to a stronger absorption capacity of a material. In some embodiments, the first absorption coefficient of each leaf of the plurality of leaves 420 may exceed the second coefficient of each interval 430 between two neighboring leaves of the plurality of leaves 420. In some embodiments, the rotary table 410 may be made of a same material as the plurality of leaves 420 to block (or shield) the radiation. For example, the rotary table 410 may be made of a radiation absorbing material having the first absorption coefficient. In some embodiments, the rotary table 410 may be made of a material different from the material of at least one of the plurality of leaves 420 (or the plurality of intervals 430). For example, the rotary table 410 may be made of any rigid material to maintain the rigidity of the shielding device 210. For example, the rotary table 410 may be made of a rigid material that may transmit the radiation and poisoned out of the transmission path of the radiation. As another example, the rotary table 410 may be made of a rigid material that may shield the radiation and at least part of the rotary table 410 may be poisoned in the transmission path of the radiation.

In some embodiments, a thickness and/or the first absorption coefficient of each leaf of the plurality of leaves 420 may be selected based on an intensity of the radiation emitted from the radiation source 110. For example, a thickness and/or the first absorption coefficient of each leaf of the plurality of leaves 420 may be determined according to Equation (1):

$$\mu(E) = -\frac{\ln\left(\frac{I}{I_0}\right)}{x}, \tag{1}$$

where $\mu(E)$ represents a first absorption coefficient of a leaf of the plurality of leaves 420, x represents a thickness of the leaf, $I_0$ represents an intensity of the radiation emitted from the radiation source 110, and I represents an intensity of the radiation being absorbed by the leaf. According to Equation (1), if the radiation source 110 emits radiation of a constant intensity, the greater the first absorption coefficient $\mu(E)$ and/or the greater the thickness x of the leaf, the lower the intensity I of the radiation being absorbed by the leaf, and the more radiation traversing the leaf. To ensure that the leaf completely shields the radiation, the greater the radiation emitted from the radiation source 110, the greater the first absorption coefficient μ(E) and/or the greater the thickness x of the leaf may be selected. Thus, the first absorption coefficient μ(E) and/or the thickness x of each leaf may be determined according to the intensity of the radiation emitted from the radiation source 110.

In some embodiments, a size of each leaf of the plurality of leaves 420 may be configured for completely shielding the radiation emitted from the radiation source 110 when the leaf is positioned in the transmission path of the radiation. For example, an area of each leaf of the plurality of leaves 420 may exceed an area of the emission window of the radiation source 110. In some embodiments, the smaller the distance between the radiation source 110 and a leaf of the plurality of leaves 420 that is configured to shield the radiation, the smaller diameter of the radiation beam impinging on the leaf, and the smaller the size of the leaf being needed to completely shield the radiation. Thus, the size of each leaf of the plurality of leaves 420 may be determined based on the distance between the radiation source 110 and the leaf of the plurality of leaves 420 that is configured to shield the radiation. In some embodiments, each of the plurality of leaves 420 may have a same size. For example, as shown in FIG. 5, the size of each of the plurality of leaves 420 may be the same. Alternatively, some leaves of the plurality of leaves 420 may have a same size, while the other leaves of the plurality of leaves 420 may have a different size.

In some embodiments, a shape of each leaf of the plurality of leaves 420 may be any suitable shape that may completely shield the radiation emitted from the radiation source 110. For example, the shape of each leaf may include a rectangle, a circle, a square, an irregular shape, or the like, or any combination thereof. In some embodiments, each of the plurality of leaves 420 may have a same shape (or a same size). For example, as shown in FIG. 5, the shape of each of the plurality of leaves 420 may be the same rectangle (or the size of each of the plurality of leaves 420 may be the same). Alternatively, some leaves of the plurality of leaves 420 may have a same shape, while the other leaves of the plurality of leaves 420 may have a different shape. For example, a shape of each of some leaves of the plurality of leaves 420 may be a rectangle, and a shape of each of the others may be irregular.

An interval 430 between two neighboring leaves of the plurality of leaves 420 may be made of a radiation permeable material to make the radiation emitted from the radiation source 110 pass or diffuse through. If the radiation emitted from the radiation source 110 is X-ray, exemplary radiation permeable material may include air, plastic, wood, blotting paper, or the like, or any combination thereof. In some embodiments, each of the plurality of intervals 430 may be made of a same material. Alternatively, some intervals of the plurality of intervals 430 may be made of a same material and the other intervals of the plurality of intervals 430 may be made of a different material. For example, some intervals of the plurality of intervals 430 may be void, while others may be made of plastic. In some embodiments, a shape of each interval of the plurality of intervals 430 may be any suitable shape that may transmit the radiation emitted from the radiation source 110 to the subject 130. For example, the shape of each interval of the plurality of intervals 430 may include a circular sector, a rectangle, a circle, a square, an irregular shape, or the like, or any combination thereof. In some embodiments, each of the plurality of intervals 430 may have a same shape (or a same size). For example, as shown in FIG. 5, the shape of each of the plurality of intervals 430 may be the same circular sector (or the size of each of the plurality of intervals 430 may be the same). Alternatively, some of the plurality of intervals 430 may have a same shape, while the others of the plurality of intervals 430 may have a different shape. For example, a shape of each of some intervals of the plurality of intervals 430 may be a rectangle, and a shape of each of the others may be a circular sector.

In some embodiments, a leaf count of the plurality of leaves 420 (or an interval count of the plurality of intervals 430) may correlate with a frequency of the produced pulsed radiation. For example, under a same rotation speed of the rotary table 410, the greater the leaf count (or the interval count), the greater frequency of the produced pulsed radiation. Thus, in some embodiments, the leaf count (or the interval count) and the rotation speed of the rotary table 410 may be determined based on the frequency of the produced pulsed radiation.

It should be noted that the description of the pulse generator 120 described in FIG. 4 or FIG. 5 is provided for the purposes of illustration, and not intended to limit the scope of the present disclosure. For persons having ordinary skills in the art, various variations and modifications may be conducted under the teaching of the present disclosure. However, those variations and modifications may not depart from the protection of the present disclosure. For example, the pulse generator 120 may include a rotary table and only one leaf (e.g., a semicircular leaf).

Figure 6:
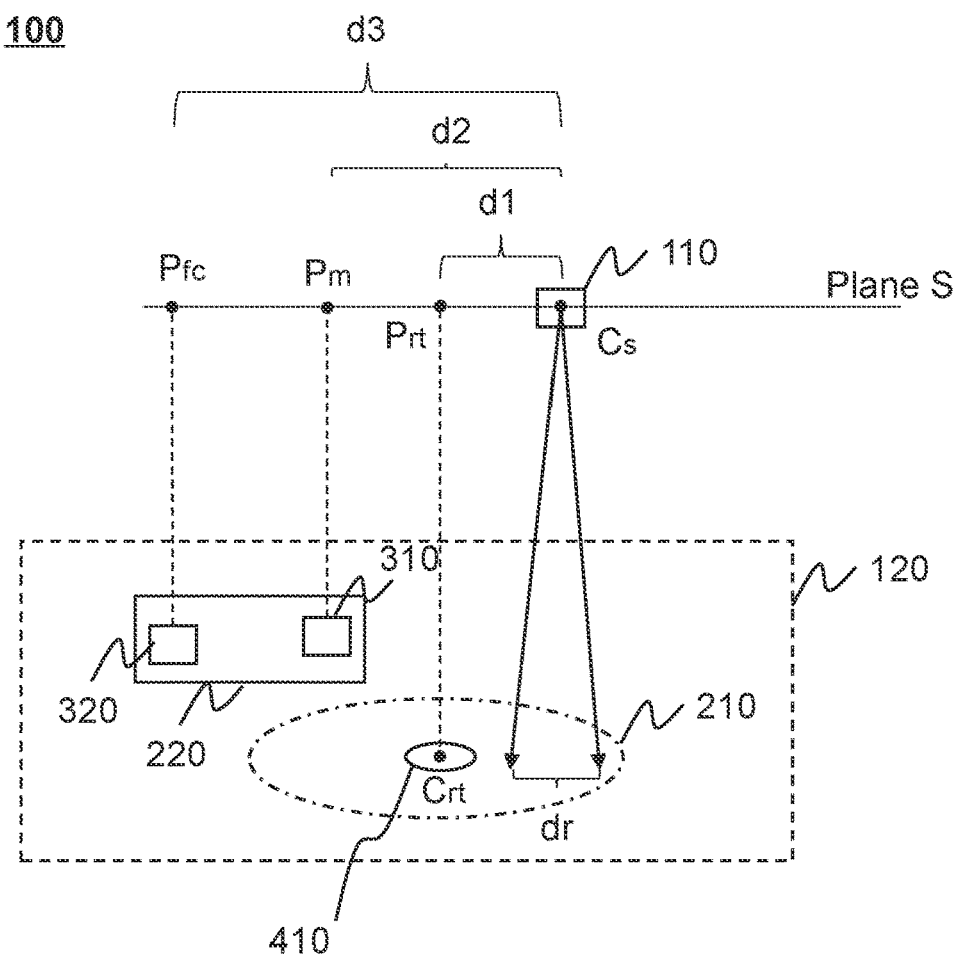

FIG. 6 is a schematic diagram illustrating an exemplary radiation system 100 according to some embodiments of the present disclosure. As shown in FIG. 6, the radiation system 100 may include a radiation source 110 and a pulse generator 120. The pulse generator 120 may include a shielding device 210 and a control device 220. The shielding device 210 may include a rotary table 410 and a plurality of leaves (not shown). The control device 220 may include a motor 310 and a frequency converter 320.

In some embodiments, the rotary table 410 may be projected onto a plane S of the radiation source 110. A projection position Prt of the center Crt of the rotary table 410 may be offset from a center Cs of the radiation source 110. For example, a first offset distance d1 between the projection position Prt of the center Crt of the rotary table 410 and the center Cs of the radiation source 110 may exceed a first distance threshold such that the rotary table 410 is not positioned in the transmission path of the radiation and therefore does not block the radiation. The projection position Prt may be a position of a projection of the center Crt of the rotary table 410 onto the plane S of the radiation source 110. As used herein, the plane S of the radiation source may be a plane of the emission window. In some embodiments, the first distance threshold may be selected based on a diameter dr of the radiation beam on a plane of the rotary table 410. For example, to prevent the rotary table 410 from shielding the radiation from the radiation source 110, the first offset distance d1 may exceed the diameter dr of the radiation beam on a plane of the rotary table 410. For example, the diameter dr is 100 mm, the first threshold distance may be designated as a value equal to or greater than 100 mm. The first offset distance d1 may exceed the designated first threshold to prevent the rotary table 410 from shielding the radiation from the radiation source 110. For example, the first threshold distance is 105 mm, and the first offset distance d1 is 108 mm.

In some embodiments, the motor 310 may be projected onto the plane S of the radiation source 110. As shown in FIG. 6, a projection position Pm of the motor 310 may be offset from the center Cs of the radiation source 110. For example, a second offset distance d2 between the projection position Pm of the motor 310 and the center Cs of the radiation source 110 may exceed a second distance threshold such that the motor 310 is not positioned in the transmission path of the radiation and therefore does not block the radiation. The projection position Pm may be a position of a projection of the center of the motor 310 onto the plane S. In some embodiments, the second distance threshold may be selected based on a diameter dr' of the radiation beam on a plane of the motor 310. For example, to prevent the motor 310 from shielding the radiation from the radiation source 110, the second offset distance d2 may exceed a diameter dr' of the radiation beam on a plane of the motor 310. For example, the diameter dr' is 100 mm, the second threshold distance may be designated as a value equal to or greater than 100 mm. The second offset distance d2 may exceed the designated second threshold to prevent the motor 310 from shielding the radiation from the radiation source 110. For example, the second threshold distance is 105 mm, and the second offset distance d2 is 108 mm.

In some embodiments, the frequency converter 320 may be projected onto the plane S of the radiation source 110. As shown in FIG. 6, a projection position Pfc of the frequency converter 320 may be offset from the center Cs of the radiation source 110. For example, a third offset distance d3 between a projection position Pfc of the frequency converter 320 and the center Cs of the radiation source 110 may exceed a third distance threshold such that the frequency converter 320 is not positioned in the transmission path of the radiation and therefore does not block the radiation. The projection position Pfc may be a position of a projection of the center of the frequency converter 320 onto the plane S. In some embodiments, the third distance threshold may be selected based on a diameter dr" of the radiation beam on a plane of the frequency converter 320. For example, to prevent the frequency converter 320 from shielding the radiation from the radiation source 110, the third offset distance d3 may exceed the diameter dr" of the radiation beam on a plane of the frequency converter 320. For example, the diameter dr" is 100 mm, the third threshold distance may be designated as a value equal to or greater than 100 mm. The third offset distance d3 may exceed the designated third threshold to prevent the frequency converter 320 from shielding the radiation from the radiation source 110. For example, the third threshold distance is 105 mm, and the third offset distance d3 is 108 mm. In some embodiments, the first threshold distance, the second threshold distance, and/or the threshold distance may be same or different. In some embodiments, the first threshold distance, the second threshold distance, and/or the threshold distance may be determined according to a size of the rotary table 410, a size of the leaves 420, a size of the motor 310, a size of the frequency converter 320, a size of the emission window of the radiation source 110, or the like, or any combination thereof.

It should be noted that the description of the radiation system 100 described in FIG. 6 is provided for the purposes of illustration, and not intended to limit the scope of the present disclosure. For persons having ordinary skills in the art, various variations and modifications may be conducted under the teaching of the present disclosure. However, those variations and modifications may not depart from the protection of the present disclosure.

Figure 7:
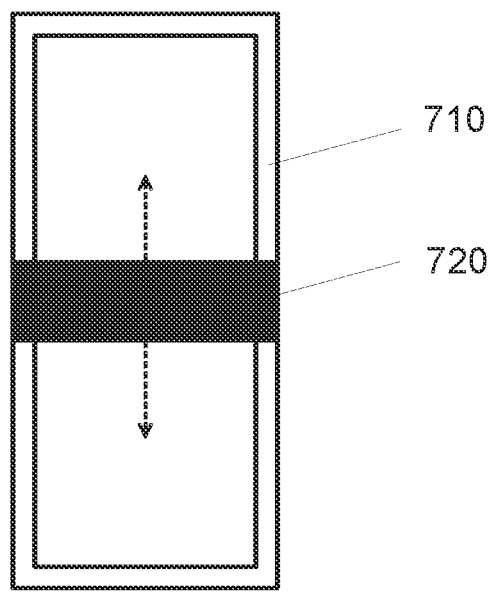

FIG. 7 is a schematic diagram illustrating an exemplary shielding device 210 according to some embodiments of the present disclosure. As shown in FIG. 7, the shielding device 210 may include a rail 710 and a leaf 720 configured to slide along the rail 710.

In some embodiments, the rail 710 may be parallel to the emission window of the radiation source 110, thereby the leaf 720 may slide on a plane parallel to the emission window of the radiation source 110. When the leaf 720 slides into the transmission path of the radiation emitted from the radiation source 110, the leaf 720 may completely shield the radiation. When the leaf 720 slides out of the transmission path of the radiation, the radiation may pass through the shielding device 210 and travel toward the subject 130. During the periodically sliding of the leaf 720 on the rail 710, pulsed radiation may be produced. In some embodiments, the rail 710 may be mounted inside the radiation system 100 (e.g., an X-ray imaging system) via a bracket.

In some embodiments, the leaf 720 may slide driven by the control device 220 (e.g., the motor 310 thereof). In some embodiments, a sliding frequency (e.g., a count of slides of the leaf 720 to the transmission path of the radiation per unit time) of the leaf 720 may correlate with a frequency of the generated pulsed radiation. For example, the greater the sliding frequency of the leaf 720 driven by the motor 310, the greater the frequency of the produced pulsed radiation.

In some embodiments, a shape of the leaf 720 may be configured for completely shielding the radiation emitted from the radiation source 110. As shown in FIG. 7, a shape of the leaf 720 may be a rectangle. Alternatively, the shape of the leaf 720 may be any suitable shape including e.g., a circle, a square, a circular sector, an irregular shape, or the like, or any combination thereof. In some embodiments, a size of the leaf 720 may be configured for completely shielding the radiation emitted from the radiation source 110. For example, an area of the leaf 720 may exceed an area of the emission window of the radiation source 110. As another example, the area of the leaf 720 may exceed a cross-sectional area of the radiation on a plane of the leaf 720.

In some embodiments, the leaf 720 may be made of a radiation impermeable material. More descriptions regarding the radiation impermeable material may be found elsewhere (e.g., FIGS. 2, 4, and 5) of the present disclosure. In some embodiments, a thickness and/or an absorption coefficient of the leaf 720 may be determined according to Equation (1) described elsewhere (e.g., FIGS. 4 and 5) of the present disclosure.

It should be noted that the description of the shielding device 210 described in FIG. 7 is provided for the purposes of illustration, and not intended to limit the scope of the present disclosure. For persons having ordinary skills in the art, various variations and modifications may be conducted under the teaching of the present disclosure. However, those variations and modifications may not depart from the protection of the present disclosure.

Figure 8:
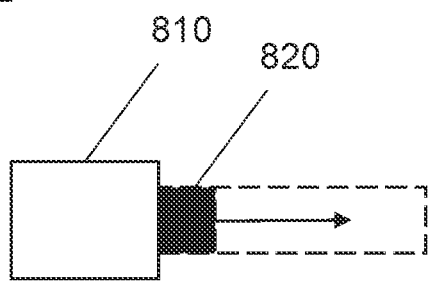

FIG. 8 is a schematic diagram illustrating an exemplary shielding device 210 according to some embodiments of the present disclosure. As shown in FIG. 8, the shielding device 210 may include a retractable module 810 and a leaf 820.

The retractable module 810 may be operably connected to the leaf 820. In some embodiments, the retractable module 810 may be controlled by the control device 220 to extend and retract the leaf 820 along a direction parallel to an emission window of the radiation source 110. When the leaf 820 extends into the transmission path of the radiation, the leaf may completely shield the radiation. When the retractable module retracts the leaf 820 out of the transmission path of the radiation, the radiation may pass through the shielding device 210 and travel toward the subject 130. During the periodically extending and retracting of the leaf 820, pulsed radiation may be produced.

In some embodiments, the retractable module 810 may be driven by the control device 220 (e.g., the motor 310 thereof). In some embodiments, an extending and retracting frequency (e.g., a count of extending of the leaf 820 to the transmission path of the radiation per unit time) of the leaf 820 may correlate with a frequency of the generated pulsed radiation. For example, the greater the extending and retracting frequency of the leaf 820 driven by the motor 310, the greater the frequency of the produced pulsed radiation.

In some embodiments, a shape of the leaf 820 may be configured for completely shielding the radiation emitted from the radiation source 110. As shown in FIG. 8, a shape of the leaf 820 may be a rectangle. Alternatively, the shape of the leaf 820 may be any suitable shape including e.g., a circle, a square, a circular sector, an irregular shape, or the like, or any combination thereof. In some embodiments, a size of the leaf 820 may be configured for completely shielding the radiation emitted from the radiation source 110. For example, an area of the leaf 820 may exceed an area of the emission window of the radiation source 110. As another example, the area of the leaf 820 may exceed a cross-sectional area of the radiation on a plane of the leaf 820.

In some embodiments, the leaf 820 may be made of a radiation impermeable material. More descriptions regarding the radiation impermeable material may be found elsewhere (e.g., FIGS. 2, 4, and 5) of the present disclosure. In some embodiments, a thickness and/or an absorption coefficient of the leaf 820 may be determined according to Equation (1) described elsewhere (e.g., FIGS. 4 and 5) of the present disclosure.

It should be noted that the description of the shielding device 210 described in FIG. 8 is provided for the purposes of illustration, and not intended to limit the scope of the present disclosure. For persons having ordinary skills in the art, various variations and modifications may be conducted under the teaching of the present disclosure. However, those variations and modifications may not depart from the protection of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±1%, ±5%, ±10%, or ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A pulse generator for a radiation source, the pulse generator comprising:
   a shielding device; and
   a control device operably connected with the shielding device, the control device being configured to control the shielding device to intermittently shield radiation emitted from the radiation source to produce pulsed radiation, wherein a surface of the shielding device is parallel to a surface of an emission window of the radiation source.

2. The pulse generator of claim 1, wherein the shielding device comprises:
   a rotary table configured to rotate about a center of the rotary table; and
   a plurality of leaves circumferentially extending from the rotary table.

3. The pulse generator of claim 2, wherein
   a leaf of the plurality of leaves has a first absorption coefficient,
   an area between two neighboring leaves of the plurality of leaves with a second absorption coefficient, and
   the first absorption coefficient is greater than the second absorption coefficient.

4. The pulse generator of claim 3, wherein the rotary table has the first absorption coefficient.

5. The pulse generator of claim 2, wherein a thickness and a first absorption coefficient of each leaf of the plurality of leaves relate to an intensity of the radiation emitted from the radiation source.

6. The pulse generator of claim 2, wherein a size of each leaf of the plurality of leaves is configured for shielding the radiation emitted from the radiation source.

7. The pulse generator of claim 2, wherein a projection position of the center of the rotary table is offset from a center of the radiation source, the projection position of the center of the rotary table being a position of a projection of the center of the rotary table onto a plane of the radiation source.

8. The pulse generator of claim 1, wherein the shielding device comprises:
   a rail parallel to an emission window of the radiation source; and
   a leaf configured to slide along the rail, the leaf being made of a radiation impermeable material.

9. The pulse generator of claim 8, wherein a size of the leaf is configured for shielding the radiation emitted from the radiation source.

10. The pulse generator of claim 1, wherein the shielding device comprises:
    a retractable module operably connected to a leaf, the retractable module being controlled by the control device to extend and retract the leaf along a direction parallel to an emission window of the radiation source, the leaf being made of a radiation impermeable material.

11. The pulse generator of claim 10, wherein a size of the leaf is configured for shielding the radiation emitted from the radiation source.

12. The pulse generator of claim 1, wherein the control device comprises:
    a motor configured to drive the shielding device, or a portion thereof, to intermittently shield the radiation emitted from the radiation source.

13. The pulse generator of claim 12, wherein a projection position of the motor projected onto a plane of the radiation source is offset from the radiation source.

14. The pulse generator of claim 12, wherein the control device further comprises:
    a frequency converter operably connected to the motor, the frequency converter being configured to control a speed of the shielding device, or a portion thereof.

15. The pulse generator of claim 14, wherein a projection position of the frequency converter projected onto a plane of the radiation source is offset from the radiation source.

16. The pulse generator of claim 1, wherein the radiation emitted from the radiation source includes X-ray, and a material of the shielding device, or a portion thereof, includes at least one of iron, tungsten, lead, a tungsten alloy, or a lead alloy.

17. A system, comprising:
a radiation source; and
a pulse generator, the pulse generator comprising:
   a shielding device; and
   a control device operably connected with the shielding device, the control device being configured to control the shielding device to intermittently shield radiations emitted from the radiation source to produce pulsed radiation,
wherein a surface of the shielding device is parallel to a surface of an emission window of the radiation source.

18. The system of claim 17, wherein the shielding device comprises:
a rotary table configured to rotate about a center of the rotary table; and
a plurality of leaves circumferentially extending from the rotary table.

19. The system of claim 18, wherein
a leaf of the plurality of leaves has a first absorption coefficient,
an area between two neighboring leaves of the plurality of leaves with a second absorption coefficient, and
the first absorption coefficient is greater than the second absorption coefficient.

20. The pulse generator of claim 1, wherein a distance between the surface of the shielding device and the surface of the emission window equals a shortest distance between the shielding device and the radiation source.

* * * * *